United States Patent
Castaneda et al.

(10) Patent No.: US 11,324,538 B2
(45) Date of Patent: May 10, 2022

(54) ACTIVE BONE PLATE

(71) Applicants: Biomet Manufacturing, LLC, Warsaw, IN (US); Driany Alfonso, Surfside, FL (US)

(72) Inventors: Alfredo Castaneda, Miami, FL (US); Cesare Cavallazzi, Miramar, FL (US); Driany Alfonso, Surfside, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 17/086,757

(22) Filed: Nov. 2, 2020

(65) Prior Publication Data

US 2021/0169536 A1   Jun. 10, 2021

Related U.S. Application Data

(60) Provisional application No. 62/943,321, filed on Dec. 4, 2019.

(51) Int. Cl.
*A61B 17/80* (2006.01)
*A61B 17/68* (2006.01)

(52) U.S. Cl.
CPC ...... *A61B 17/8047* (2013.01); *A61B 17/8014* (2013.01); *A61B 2017/681* (2013.01)

(58) Field of Classification Search
CPC . A61B 17/80; A61B 17/8014; A61B 17/8033; A61B 17/8047; A61B 17/8052; A61B 17/8057
See application file for complete search history.

(56) References Cited

U.S. PATENT DOCUMENTS

| 2,406,832 A | 9/1946 | Hardinge |
| 2,580,821 A | 1/1952 | Toufick |
| 3,807,394 A | 4/1974 | Attenborough |

(Continued)

FOREIGN PATENT DOCUMENTS

| CA | 2863597 A1 | 8/2013 |
| CN | 101060815 A | 10/2007 |

(Continued)

OTHER PUBLICATIONS

"U.S. Appl. No. 13/166,539, Final Office Action dated May 21, 2014", 9 pgs.

(Continued)

*Primary Examiner* — Larry E Waggle, Jr.
(74) *Attorney, Agent, or Firm* — Schwegman Lundberg & Woessner, P.A.

(57) ABSTRACT

Disclosed herein are bone plates, bone plate systems, and methods of use thereof that can include a bone plate that includes a plate frame and first and second anvils. The plate frame can have a first surface and define a first opening and a second opening. Each of the first and second anvils can include first and second plates, and a body located in between the first and second plates. The first plate can have a first surface arranged to rest against the first surface of the plate frame when the bone plate is implanted. The second plate can be sized to pass into each of the first and second openings. The body can define a through hole sized to receive a fastener. When the bone plate is implanted, the plate frame can be moveable relative to the first and second anvils.

20 Claims, 7 Drawing Sheets

(56) References Cited

U.S. PATENT DOCUMENTS

| | | | |
|---|---|---|---|
| 4,029,091 A | 6/1977 | Von Bezold et al. |
| 4,338,296 A | 7/1982 | Lobmann et al. |
| 4,361,153 A | 11/1982 | Slocum et al. |
| 4,743,260 A | 5/1988 | Burton |
| 4,905,679 A | 3/1990 | Morgan |
| 4,943,292 A | 7/1990 | Foux |
| 5,306,310 A | 4/1994 | Siebels |
| 5,423,816 A | 6/1995 | Lin |
| 5,468,242 A | 11/1995 | Reisberg |
| 5,578,034 A | 11/1996 | Estes |
| 5,578,036 A | 11/1996 | Stone et al. |
| 5,681,311 A | 10/1997 | Foley et al. |
| 5,709,686 A | 1/1998 | Talos et al. |
| 5,741,258 A | 4/1998 | Klaue et al. |
| 5,743,913 A | 4/1998 | Wellisz |
| 5,984,925 A | 11/1999 | Apgar |
| 6,093,188 A | 7/2000 | Murray et al. |
| 6,206,882 B1 | 3/2001 | Cohen |
| 6,340,632 B1 | 1/2002 | Fukada et al. |
| 6,364,881 B1 | 4/2002 | Apgar et al. |
| 6,540,746 B1 | 4/2003 | Buhler et al. |
| 6,663,632 B1 | 12/2003 | Frigg |
| 6,755,832 B2 | 6/2004 | Happomem et al. |
| 6,986,771 B2 | 1/2006 | Paul et al. |
| 6,989,011 B2 | 1/2006 | Paul et al. |
| 7,048,739 B2 | 5/2006 | Konieczynski et al. |
| 7,175,624 B2 | 2/2007 | Konieczynski et al. |
| 7,189,237 B2 | 3/2007 | Huebner |
| 7,276,070 B2 | 10/2007 | Mückter |
| 7,341,591 B2 | 3/2008 | Grinberg |
| 7,377,921 B2 | 5/2008 | Studer et al. |
| 7,452,370 B2 | 11/2008 | Anderson |
| 7,572,282 B2 | 8/2009 | Boomer et al. |
| 7,591,840 B2 | 9/2009 | Suddaby |
| D603,503 S | 11/2009 | Kriska et al. |
| D603,504 S | 11/2009 | Kriska et al. |
| D603,505 S | 11/2009 | Kriska et al. |
| D603,507 S | 11/2009 | Kriska et al. |
| D603,508 S | 11/2009 | Kriska et al. |
| D603,510 S | 11/2009 | Kriska et al. |
| D603,511 S | 11/2009 | Kriska et al. |
| D603,961 S | 11/2009 | Kriska et al. |
| D603,962 S | 11/2009 | Kriska et al. |
| D603,963 S | 11/2009 | Kriska et al. |
| D603,964 S | 11/2009 | Kriska et al. |
| 7,621,942 B2 | 11/2009 | Piehl |
| 7,641,675 B2 | 1/2010 | Lindemann et al. |
| 7,651,517 B2 | 1/2010 | Konieczynski et al. |
| 7,749,257 B2 | 7/2010 | Medoff |
| 7,806,914 B2 | 10/2010 | Boyd et al. |
| 7,811,312 B2 | 10/2010 | Stevens et al. |
| 7,833,256 B2 | 11/2010 | Biedermann et al. |
| 7,842,037 B2 | 11/2010 | Schulze |
| 7,887,569 B2 | 2/2011 | Frigg |
| 7,887,587 B2 | 2/2011 | Griffiths et al. |
| 7,914,561 B2 | 3/2011 | Konieczynski et al. |
| 8,486,070 B2 | 7/2013 | Morgan et al. |
| 8,687,865 B2 | 4/2014 | Wilson et al. |
| 8,790,379 B2 * | 7/2014 | Bottlang ............ A61B 17/8004 606/289 |
| 8,882,815 B2 | 11/2014 | Bottlang et al. |
| 8,992,583 B2 | 3/2015 | Bottlang et al. |
| 9,101,423 B2 | 8/2015 | Hulliger |
| 9,295,508 B2 * | 3/2016 | Bottlang ............ A61B 17/8028 |
| 9,510,879 B2 | 12/2016 | Bottlang et al. |
| 9,700,361 B2 | 7/2017 | Bottlang et al. |
| 9,763,713 B2 | 9/2017 | Bottlang et al. |
| 9,788,873 B2 | 10/2017 | Bottlang et al. |
| 10,022,168 B2 | 7/2018 | Bottlang et al. |
| 10,070,905 B2 | 9/2018 | Bottlang et al. |
| 10,507,049 B2 | 12/2019 | Bottlang et al. |
| 10,716,605 B2 | 7/2020 | Bottlang et al. |
| 2002/0150671 A1 | 10/2002 | Koulik et al. |
| 2004/0006343 A1 | 1/2004 | Sevrain |
| 2004/0019353 A1 | 1/2004 | Freid et al. |
| 2004/0097937 A1 | 5/2004 | Pike et al. |
| 2004/0193155 A1 | 9/2004 | Castaneda |
| 2004/0220570 A1 | 11/2004 | Frigg |
| 2005/0090825 A1 | 4/2005 | Pfefferle et al. |
| 2005/0096657 A1 | 5/2005 | Autericque et al. |
| 2005/0116930 A1 | 6/2005 | Gates |
| 2005/0196421 A1 | 9/2005 | Hunter et al. |
| 2005/0216008 A1 | 9/2005 | Zwirnmann et al. |
| 2005/0273105 A1 | 12/2005 | Konieczynski et al. |
| 2005/0288668 A1 | 12/2005 | Brinkhaus |
| 2006/0058796 A1 | 3/2006 | Hartdegen et al. |
| 2006/0116682 A1 | 6/2006 | Longo |
| 2006/0155282 A1 | 7/2006 | Vese |
| 2006/0195099 A1 | 8/2006 | Bottlang |
| 2006/0241612 A1 | 10/2006 | Medoff |
| 2006/0247638 A1 | 11/2006 | Trieu et al. |
| 2006/0247639 A1 | 11/2006 | Anderson |
| 2006/0264949 A1 | 11/2006 | Kohut et al. |
| 2007/0055251 A1 | 3/2007 | Huebner et al. |
| 2007/0118127 A1 | 5/2007 | Serhan et al. |
| 2007/0213729 A1 | 9/2007 | Lindemann et al. |
| 2008/0027439 A1 | 1/2008 | Sasing |
| 2008/0083613 A1 | 4/2008 | Oi et al. |
| 2008/0097445 A1 | 4/2008 | Weinstein |
| 2008/0147122 A1 | 6/2008 | Jackson |
| 2008/0147125 A1 | 6/2008 | Colleran et al. |
| 2008/0154265 A1 | 6/2008 | Duda et al. |
| 2008/0200955 A1 | 8/2008 | Tepic |
| 2008/0275509 A1 | 11/2008 | Clifford et al. |
| 2008/0306536 A1 | 12/2008 | Frigg et al. |
| 2009/0012571 A1 | 1/2009 | Perrow et al. |
| 2009/0030467 A1 | 1/2009 | Sonohata et al. |
| 2009/0036930 A1 | 2/2009 | Allison |
| 2009/0043341 A1 | 2/2009 | Tyber et al. |
| 2009/0062915 A1 | 3/2009 | Kohm et al. |
| 2009/0118768 A1 | 5/2009 | Sixto, Jr. et al. |
| 2009/0118769 A1 | 5/2009 | Sixto, Jr. et al. |
| 2009/0118770 A1 | 5/2009 | Sixto, Jr. et al. |
| 2009/0125067 A1 | 5/2009 | Mazzuca et al. |
| 2009/0125069 A1 | 5/2009 | Sixto, Jr. et al. |
| 2009/0125070 A1 | 5/2009 | Sixto, Jr. et al. |
| 2009/0157121 A1 | 6/2009 | Harris et al. |
| 2009/0157123 A1 | 6/2009 | Appenzeller et al. |
| 2009/0222049 A1 | 9/2009 | Frigg et al. |
| 2009/0234393 A1 | 9/2009 | Sournac et al. |
| 2009/0270924 A1 | 10/2009 | Wing et al. |
| 2009/0318921 A1 | 12/2009 | White et al. |
| 2009/0318976 A1 | 12/2009 | Gabriel et al. |
| 2010/0010541 A1 | 1/2010 | Boomer et al. |
| 2010/0036430 A1 | 2/2010 | Hartdegen et al. |
| 2010/0076495 A1 | 3/2010 | Lindemann et al. |
| 2010/0094351 A1 | 4/2010 | Haggenmaker et al. |
| 2010/0114177 A1 | 5/2010 | Piehl |
| 2010/0131012 A1 | 5/2010 | Ralph et al. |
| 2010/0131013 A1 | 5/2010 | Ralph et al. |
| 2010/0217327 A1 | 8/2010 | Vancelette et al. |
| 2010/0249850 A1 | 9/2010 | Cerynik et al. |
| 2010/0305569 A1 | 12/2010 | Leuenberger et al. |
| 2011/0029024 A1 | 2/2011 | Crainich |
| 2011/0118742 A1 | 5/2011 | Hulliger et al. |
| 2011/0319942 A1 | 12/2011 | Bottlang et al. |
| 2012/0143193 A1 | 6/2012 | Hulliger |
| 2012/0277746 A1 | 11/2012 | Morgan et al. |
| 2012/0310289 A1 | 12/2012 | Bottland et al. |
| 2013/0000631 A1 | 1/2013 | Bottlang et al. |
| 2013/0204304 A1 | 8/2013 | Bottlang et al. |
| 2014/0330275 A1 | 11/2014 | Bottlang et al. |
| 2015/0025588 A1 | 1/2015 | Bottlang et al. |
| 2015/0230840 A1 | 8/2015 | Bottlang et al. |
| 2015/0327896 A1 | 11/2015 | Bottlang et al. |
| 2016/0074082 A1 * | 3/2016 | Cremer ............ A61B 17/8085 606/70 |
| 2016/0081729 A1 | 3/2016 | Velikov et al. |
| 2016/0157905 A1 | 6/2016 | Arellano et al. |
| 2016/0166293 A1 | 6/2016 | Bottlang et al. |
| 2017/0273728 A1 | 9/2017 | Bottlang et al. |
| 2018/0036048 A1 | 2/2018 | Bottlang et al. |

(56) References Cited

U.S. PATENT DOCUMENTS

| | | | |
|---|---|---|---|
| 2018/0070997 | A1 | 3/2018 | Bottlang et al. |
| 2020/0155209 | A1 | 5/2020 | Bottlang et al. |

FOREIGN PATENT DOCUMENTS

| | | | |
|---|---|---|---|
| CN | 101262828 A | 9/2008 | |
| CN | 101291634 A | 10/2008 | |
| CN | 104135953 A | 11/2014 | |
| CN | 106794036 A | 5/2017 | |
| CN | 108186101 A | 6/2018 | |
| EP | 0615728 A2 | 9/1994 | |
| EP | 1926445 A1 | 6/2008 | |
| EP | 2005978 A1 | 12/2008 | |
| EP | 1926445 B1 | 5/2013 | |
| FR | 742618 A | 1/1933 | |
| FR | 2634368 A1 | 1/1990 | |
| JP | 2005507953 A | 3/2005 | |
| JP | 2009501575 A | 1/2009 | |
| JP | 2009505751 A | 2/2009 | |
| JP | 2010521274 A | 6/2010 | |
| JP | 2015507953 A | 3/2015 | |
| JP | 2017521189 A | 8/2017 | |
| JP | 2018064962 A | 4/2018 | |
| WO | WO-2005065557 A1 | 7/2005 | |
| WO | WO-2007009124 A2 | 1/2007 | |
| WO | WO-2007056874 A1 | 5/2007 | |
| WO | WO-2009039430 A1 | 3/2009 | |
| WO | WO-2010037984 A1 | 4/2010 | |
| WO | WO-2010111350 A1 | 9/2010 | |
| WO | WO-2010132252 A1 | 11/2010 | |
| WO | WO-2011163387 A2 | 12/2011 | |
| WO | WO-2013021357 A1 | 2/2013 | |
| WO | WO-2013116642 A1 | 8/2013 | |
| WO | WO-2016014977 A1 | 1/2016 | |

OTHER PUBLICATIONS

"U.S. Appl. No. 13/166,539, Non Final Office Action dated Jan. 2, 2014", 10 pgs.
"U.S. Appl. No. 13/166,539, Non Final Office Action dated Jun. 28, 2013", 10 pgs.
"U.S. Appl. No. 13/166,539, Notice of Allowability dated Oct. 9, 2014", 4 pgs.
"U.S. Appl. No. 13/166,539, Notice of Allowance dated Aug. 15, 2014", 7 pgs.
"U.S. Appl. No. 13/166,539, Notice of Non-compliant Amendment dated Feb. 20, 2014", 3 pgs.
"U.S. Appl. No. 13/166,539, Preliminary Amendment filed Jul. 19, 2012", 7 pgs.
"U.S. Appl. No. 13/166,539, Response filed Jan. 28, 2014 to Non Final Office Action dated Jan. 2, 2014", 3 pgs.
"U.S. Appl. No. 13/166,539, Response filed May 2, 2014 to Non Final Office Action dated Jan. 2, 2014", 14 pgs.
"U.S. Appl. No. 13/166,539, Response filed May 2, 2014 to Non Final Office Action dated Feb. 20, 2014", 14 pgs.
"U.S. Appl. No. 13/166,539, Response filed May 6, 2013 to Restriction Requirement dated Mar. 5, 2013", 9 pgs.
"U.S. Appl. No. 13/166,539, Response filed Jul. 21, 2014 to Final Office Action dated May 21, 2014", 13 pgs.
"U.S. Appl. No. 13/166,539, Response filed Oct. 28, 2013 to Non Final Office Action dated Jun. 28, 2013", 10 pgs.
"U.S. Appl. No. 13/166,539, Restriction Requirement dated Mar. 5, 13", 6 pgs.
"U.S. Appl. No. 13/490,249, Amendment filed Jan. 28, 2014", 3 pgs.
"U.S. Appl. No. 13/490,249, Non Final Office Action dated Sep. 19, 2013", 10 pgs.
"U.S. Appl. No. 13/490,249, Notice of Allowance dated Mar. 27, 2014", 7 pgs.
"U.S. Appl. No. 13/490,249, Response filed Jan. 21, 2014 to Non Final Office Action dated Sep. 19, 2013", 12 pgs.
"U.S. Appl. No. 13/490,249, Response filed May 7, 2013 to Restriction Requirement dated Mar. 7, 2013", 11 pgs.
"U.S. Appl. No. 13/490,249, Response filed Sep. 3, 2013 to Restriction Requirement dated Jul. 2, 2013", 6 pgs.
"U.S. Appl. No. 13/490,249, Restriction Requirement dated Mar. 7, 2013", 7 pgs.
"U.S. Appl. No. 13/490,249, Restriction Requirement dated Jul. 2, 2013", 8 pgs.
"U.S. Appl. No. 13/554,119, Advisory Action dated Feb. 12, 2014", 2 pgs.
"U.S. Appl. No. 13/554,119, Final Office Action dated Sep. 19, 2013", 9 pgs.
"U.S. Appl. No. 13/554,119, Non Final Office Action dated Mar. 13, 2013", 6 pgs.
"U.S. Appl. No. 13/554,119, Non Final Office Action dated Jul. 16, 2014", 7 pgs.
"U.S. Appl. No. 13/554,119, Notice of Allowance dated Nov. 24, 2014", 5 pgs.
"U.S. Appl. No. 13/554,119, Preliminary Amendment filed Jun. 20, 2012", 5 pgs.
"U.S. Appl. No. 13/554,119, Response filed Jan. 28, 2014 to Final Office Action dated Sep. 19, 2013", 3 pgs.
"U.S. Appl. No. 13/554,119, Response filed Mar. 19, 2014 to Advisory Action dated Feb. 12, 2014", 13 pgs.
"U.S. Appl. No. 13/554,119, Response filed Aug. 13, 2013 to Non Final Office Action dated Mar. 13, 2013", 8 pgs.
"U.S. Appl. No. 13/554,119, Response filed Oct. 16, 2014 to Non Final Office Action dated Jul. 16, 2014", 12 pgs.
"U.S. Appl. No. 13/755,493, Advisory Action dated Dec. 4, 2015", 4 pgs.
"U.S. Appl. No. 13/755,493, Examiner Interview Summary dated Dec. 4, 2015", 1 pg.
"U.S. Appl. No. 13/755,493, Final Office Action dated Jul. 9, 2015", 12 pgs.
"U.S. Appl. No. 13/755,493, Non Final Office Action dated Nov. 19, 2014", 13 pgs.
"U.S. Appl. No. 13/755,493, Notice of Allowance dated Dec. 23, 2015", 5 pgs.
"U.S. Appl. No. 13/755,493, Preliminary Amendment dated Jan. 28, 2014", 3 pgs.
"U.S. Appl. No. 13/755,493, Response filed Feb. 19, 2015 to Non-Final Office Action dated Nov. 19, 2014", 16 pgs.
"U.S. Appl. No. 13/755,493, Response filed Oct. 28, 2014 to Restriction Requirement dated Oct. 9, 2014", 9 pgs.
"U.S. Appl. No. 13/755,493, Response filed Nov. 12, 2015 to Final Office Action dated Jul. 9, 2015", 15 pgs.
"U.S. Appl. No. 13/755,493, Response filed Dec. 9, 2015 to Advisory Action dated Dec. 4, 2015", 12 pgs.
"U.S. Appl. No. 13/755,493, Restriction Requirement dated Oct. 9, 2014", 6 pgs.
"U.S. Appl. No. 13/755,493, Supplemental Preliminary Amendment dated Jan. 30, 2014", 3 pgs.
"U.S. Appl. No. 14/308,286, Corrected Notice of Allowance dated Jun. 28, 2016", 4 pgs.
"U.S. Appl. No. 14/308,286, Notice of Allowance dated Mar. 23, 2016", 8 pgs.
"U.S. Appl. No. 14/308,286, Notice of Allowance dated Aug. 5, 2016", 7 pgs.
"U.S. Appl. No. 14/308,286, Preliminary Amendment filed Sep. 17, 2014", 7 pgs.
"U.S. Appl. No. 14/308,314, Final Office Action dated Aug. 25, 2016", 8 pgs.
"U.S. Appl. No. 14/308,314, Non Final Office Action dated Feb. 7, 2017", 9 pgs.
"U.S. Appl. No. 14/308,314, Non Final Office Action dated Mar. 23, 2016", 9 pgs.
"U.S. Appl. No. 14/308,314, Notice of Allowance dated Jun. 12, 2017", 5 pgs.
"U.S. Appl. No. 14/308,314, Preliminary Amendment filed Sep. 17, 2014", 7 pgs.
"U.S. Appl. No. 14/308,314, Response filed May 8, 2017 to Non Final Office Action dated Feb. 7, 2017", 12 pgs.

(56) References Cited

OTHER PUBLICATIONS

"U.S. Appl. No. 14/308,314, Response filed Jul. 25, 2016 to Non Final Office Action dated Mar. 23, 2016", 11 pgs.
"U.S. Appl. No. 14/308,314, Response filed Nov. 23, 2016 to Final Office Action dated Aug. 25, 2016", 10 pgs.
"U.S. Appl. No. 14/630,938, Final Office Action dated Dec. 20, 2016", 5 pgs.
"U.S. Appl. No. 14/630,938, Non Final Office Action dated Aug. 9, 2016", 14 pgs.
"U.S. Appl. No. 14/630,938, Notice of Allowance dated Mar. 27, 2017", 5 pgs.
"U.S. Appl. No. 14/630,938, Notice of Allowance dated May 19, 2017", 7 pgs.
"U.S. Appl. No. 14/630,938, Preliminary Amendment filed Oct. 19, 2015", 7 pgs.
"U.S. Appl. No. 14/630,938, Response filed Feb. 28, 2017 to Final Office Action dated Dec. 20, 2016", 11 pgs.
"U.S. Appl. No. 14/630,938, Response filed Nov. 9, 2016 to Non Final Office Action dated Aug. 9, 2016", 16 pgs.
"U.S. Appl. No. 14/808,773, Non Final Office Action dated Nov. 17, 2017", 7 pgs.
"U.S. Appl. No. 14/808,773, Notice of Allowability dated Aug. 8, 2018", 8 pgs.
"U.S. Appl. No. 14/808,773, Notice of Allowance dated Apr. 11, 2018", 8 pgs.
"U.S. Appl. No. 14/808,773, Preliminary Amendment Filed Feb. 9, 2017", 3 pgs.
"U.S. Appl. No. 14/808,773, Response filed Feb. 19, 2018 to Non Final Office Action dated Nov. 17, 2017", 7 pgs.
"U.S. Appl. No. 15/047,702, Notice of Allowance dated Feb. 7, 2017", 5 pgs.
"U.S. Appl. No. 15/047,702, Notice of Allowance dated May 25, 2017", 6 pgs.
"U.S. Appl. No. 15/047,702, Notice of Allowance dated Oct. 7, 2016", 5 pgs.
"U.S. Appl. No. 15/047,702, PTO Response to Rule 312 Communication dated Feb. 17, 2017", 2 pgs.
"U.S. Appl. No. 15/616,608, Corrected Notice of Allowance dated Mar. 28, 2018", 4 pgs.
"U.S. Appl. No. 15/616,608, Non Final Office Action dated Oct. 19, 2017", 5 pgs.
"U.S. Appl. No. 15/616,608, Notice of Allowance dated Mar. 13, 2018", 5 pgs.
"U.S. Appl. No. 15/616,608, Preliminary Amendment filed Jun. 23, 2017", 7 pgs.
"U.S. Appl. No. 15/616,608, Response filed Jan. 19, 2018 to Non Final Office Action dated Oct. 19, 2017", 8 pgs.
"U.S. Appl. No. 15/684,607, Final Office Action dated Nov. 18, 2019", 5 pgs.
"U.S. Appl. No. 15/684,607, Non Final Office Action dated Aug. 2, 2019", 10 pgs.
"U.S. Appl. No. 15/684,607, Notice of Allowance dated Mar. 11, 2020", 7 pgs.
"U.S. Appl. No. 15/684,607, Response filed Jan. 20, 2020 to Final Office Action dated Nov. 18, 2019", 9 pgs.
"U.S. Appl. No. 15/684,607, Response Filed Nov. 4, 2019 to Non-Final Office Action dated Aug. 2, 2019", 10 pgs.
"U.S. Appl. No. 15/712,967, Corrected Notice of Allowability dated Oct. 16, 2019", 2 pgs.
"U.S. Appl. No. 15/712,967, Final Office Action dated Jul. 3, 2018", 11 pgs.
"U.S. Appl. No. 15/712,967, Non Final Office Action dated Feb. 19, 2019", 7 pgs.
"U.S. Appl. No. 15/712,967, Non Final Office Action dated Feb. 23, 2018", 5 pgs.
"U.S. Appl. No. 15/712,967, Notice of Allowance dated Aug. 13, 2019", 5 pgs.
"U.S. Appl. No. 15/712,967, Response filed May 20, 2019 to Non Final Office Action dated Feb. 19, 2019", 11 pgs.
"U.S. Appl. No. 15/712,967, Response filed May 23, 2018 to Non Final Office Action dated Feb. 23, 2018", 9 pgs.
"U.S. Appl. No. 15/712,967, Response Filed Oct. 3, 2018 to Final Office Action dated Jul. 3, 2018", 13 pgs.
"Australian Application Serial No. 2011270934, First Examiner Report dated Sep. 12, 2013", 4 pgs.
"Australian Application Serial No. 2011270934, Response filed Jun. 30, 2014 to First Examiner Report dated Sep. 12, 2013", 20 pgs.
"Australian Application Serial No. 2013214894, Amendment filed Mar. 8, 2017", 2 pgs.
"Australian Application Serial No. 2013214894, First Examiner Report dated Oct. 6, 2016", 3 pgs.
"Australian Application Serial No. 2013214894, Response Filed Mar. 3, 2017 to Office Action dated Oct. 6, 2017", 17 pgs.
"Australian Application serial No. 2014265031, Non Final Office Action dated Sep. 21, 2015", 3 pgs.
"Australian Application Serial No. 2014265031, Preliminary Amendment filed Jan. 28, 2015", 13 pgs.
"Australian Application Serial No. 2015292319, First Examination Report dated May 17, 2018", 3 pgs.
"Australian Application Serial No. 2015292319, Response filed Jul. 20, 2018 to First Examination Report dated May 17, 2018", 22 pgs.
"Australian Application Serial No. 2015292319, Subsequent Examiners Report dated Aug. 16, 2018", 2 pgs.
"Australian Application Serial No. 2016203422, First Examiners Report dated Oct. 19, 2016", 4 pgs.
"Australian Application Serial No. 2016203422, Response Filed Mar. 2, 2017 to Office Action dated Oct. 19, 2016", 9 pgs.
"Australian Application Serial No. 2017204637, First Examination Report dated Sep. 17, 2018", 3 pgs.
"Canadian Application Serial No. 2,803,585, Office Action dated Jan. 25, 2017", 4 pgs.
"Canadian Application Serial No. 2,803,585, Office Action dated Jul. 26, 2018", 4 pgs.
"Canadian Application Serial No. 2,803,585, Office Action dated Oct. 23, 2017", 4 pgs.
"Canadian Application Serial No. 2,803,585, Response Filed Jan. 25, 2019 to Office Action dated Jul. 26, 2018", 8 pgs.
"Canadian Application Serial No. 2,803,585, Response filed Apr. 2019, 18 to Office Action dated Oct. 23, 2017", 6 pgs.
"Canadian Application Serial No. 2,803,585, Response filed Jul. 25, 2017 to Office Action dated Jan. 25, 2017", 14 pgs.
"Canadian Application Serial No. 2,955,718, Examiner's Rule 30(2) Requisition dated Jul. 10, 2018", 4 pgs.
"Canadian Application Serial No. 2,955,718, Response Filed Jan. 10, 2019 to Examiner's Rule 30(2) Requisition dated Jul. 10, 2018", 7 pgs.
"Chinese Application Serial No. 201380011448.7, Office Action dated May 23, 2017", with English translation, 4 pages.
"Chinese Application Serial No. 201380011448.7, Office Action dated Oct. 27, 2016", with English translation, 19 pages.
"Chinese Application Serial No. 201380011448.7, Office Action dated Dec. 25, 2015", with English translation, 27 pages.
"Chinese Application Serial No. 201380011448.7, Response filed Jan. 11, 2017 to Office Action dated Oct. 27, 2016", with English claims, 10 pages.
"Chinese Application Serial No. 201380011448.7, Response filed Jul. 8, 2016 to Office Action dated Dec. 25, 2015", with English claims, 11 pages.
"Chinese Application Serial No. 201380011448.7, Response filed Jul. 24, 2017 to Office Action dated May 23, 2017", with English claims, 8 pages.
"Chinese Application Serial No. 201580047595.9, Office Action dated Aug. 29, 2018", with English translation, 16 pages.
"Chinese Application Serial No. 201580047595.9, Office Action dated Dec. 13, 2018", with English translation, 10 pages.
"Chinese Application Serial No. 201580047595.9, Response filed Oct. 12, 2018 to Office Action dated Aug. 29, 2018", with English claims, 9 pages.
"Chinese Application Serial No. 201810151451.3, Office Action dated Mar. 31, 2020", with English translation, 21 pages.

(56) References Cited

OTHER PUBLICATIONS

"Chinese Application Serial No. 201810151451.3, Response filed Aug. 12, 2020 to Office Action dated Mar. 31, 2020", with English claims, 7 pages.
"European Application Serial No. 11798862.6, Communication Pursuant to Article 94(3) EPC dated May 19, 2017", 10 pgs.
"European Application Serial No. 11798862.6, Extended European Search Report dated Mar. 16, 2015", 12 pgs.
"European Application Serial No. 11798862.6, Office Action dated Feb. 1, 2013", 2 pgs.
"European Application Serial No. 11798862.6, Response filed Jul. 30, 2013 to Office Action dated Feb. 1, 2013", 8 pgs.
"European Application Serial No. 11798862.6, Response filed Sep. 25, 2017 to Communication Pursuant to Article 94(3) EPC dated May 19, 2017", 15pgs.
"European Application Serial No. 11798862.6, Response filed Oct. 8, 2015 to Extended European Search Report dated Mar. 16, 2015", 9 pgs.
"European Application Serial No. 13743819.8, Communication Pursuant to Article 94(3) EPC dated Sep. 20, 2017", 6 pgs.
"European Application Serial No. 13743819.8, Extended European Search Report dated Nov. 11, 2015", 9 pgs.
"European Application Serial No. 13743819.8, Preliminary Amendment filed Mar. 26, 2015", 11 pgs.
"European Application Serial No. 13743819.8, Response filed Jan. 30, 2018 to Communication Pursuant to Article 94(3) EPC dated Sep. 20, 2017", 14 pgs.
"European Application Serial No. 15745735.9, Response filed Sep. 19, 2017 to Office Action dated Mar. 9, 2017", 13pgs.
"European Application Serial No. 19158141.2, Extended European Search Report dated Mar. 13, 2020", 13 pgs.
"European Application Serial No. 19158141.2, Response filed Oct. 22, 2020 to Extended European Search Report dated Mar. 13, 2020", 16 pgs.
"Indian Application Serial No. 293/DELNP/2013, First Examination Report dated Jul. 17, 2019", with English translation, 10 pages.
"International Application Serial No. PCT/US2011/041484, International Preliminary Report on Patentability dated Jan. 10, 2013", 6 pgs.
"International Application Serial No. PCT/US2011/041484, International Search Report dated Feb. 17, 2012", 4 pgs.
"International Application Serial No. PCT/US2011/041484, Written Opinion dated Feb. 17, 2012", 4 pgs.
"International Application Serial No. PCT/US2013/024336, International Preliminary Report on Patentability dated Aug. 14, 2014", 10 pgs.
"International Application Serial No. PCT/US2013/024336, International Search Report dated May 15, 2013", 4 pgs.
"International Application Serial No. PCT/US2013/024336, Written Opinion dated May 15, 2013", 8 pgs.
"International Application Serial No. PCT/US2015/042057, International Preliminary Report on Patentability dated Feb. 9, 2017", 8 pgs.
"International Application Serial No. PCT/US2015/042057, International Search Report dated Oct. 16, 2015", 4 pgs.
"International Application Serial No. PCT/US2015/042057, Written Opinion dated Oct. 16, 2015", 6 pgs.
"Japanese Application Serial No. 2014-555748, Examiners Decision of Final Refusal dated Aug. 8, 2017", with English translation, 8 pages.
"Japanese Application Serial No. 2014-555748, Notification of Reasons for Refusal dated Feb. 26, 2019", with English translation, 5 pages.
"Japanese Application Serial No. 2014-555748, Office Action dated Nov. 15, 2016", with English translation, 6 pages.
"Japanese Application Serial No. 2014-555748, Response filed Feb. 15, 2017 to Office Action dated Nov. 15, 2016", with English claims, 14 pages.
"Japanese Application Serial No. 2014-555748, Response filed May 10, 2019 to Notification of Reasons for Refusal dated Feb. 26, 2019", with English claims, 5 pages.
"Japanese Application Serial No. 2014-555748, Response filed Dec. 17, 2017 to Examiners Decision of Final Refusal dated Aug. 8, 2017", with English claims, 13 pages.
"Japanese Application Serial No. 2017-234039, Notification of Reasons for Rejection dated Dec. 18, 2018", with English translation, 4 pages.
"Japanese Application Serial No. 2017-504059, Examiners Decision of Final Refusal dated Sep. 25, 2018", with English translation, 5 pages.
"Japanese Application Serial No. 2017-504059, Notification of Reasons for Rejection dated Jun. 5, 2018", with English translation, 7 pages.
"Japanese Application Serial No. 2017-504059, Response filed Sep. 19, 2018 to Notification of Reasons for Rejection dated Jun. 5, 2018", with English claims, 14 pages.
"Standard specification for wrought titanium-6Aluminum-4Vanadium ELI (Extra Low Interstitial) alloy for surgical implant application. (UNS R56401)", ASTM F136-11, (2003), 5 pgs.
"Standard Test Methods For Equipment and Procedures Used in Evaluating the Performance Characteristics of Protective Headgear. Impact Test Apparatus.", ASMT F1446-13, (2013), 12 pgs.
Beaupre, G. S, et al., "A Comparison of Unicortical and Bicortical End Screw Attachment of Fracture Fixation Plates", Journal of Orthopaedic Trauma 6(3), (Feb. 1992), 294-300.
Bottlang, et al., "A Nonlocking End Screw Can Decrease Fracture Risk Caused by Locked Plating in the Osteoporotic Diaphysis", Journal of Bone & Joint Surgery, vol. 91, (2009), 620-627.
Bottlang, et al., "Effects of Construct Stiffness on Healing of Fractures Stabilzed with Locking Plates", Journal of Bone & Joint Surgery, vol. 92, (2010), 12-22.
Davenport, Stephen R, et al., "Dynamic Compression Plate Fixation: A Biomechanical Comparison of Unicortical vs Bicortical Distal Screw Fixation", Journal of Orthopaedic Trauma 2(2), (Feb. 1988), 146-150.
Egol, Kenneth A, et al., "Biomechanics of Locked Plates and Screws", Journal of Orthopaedic Trauma 18(8), (Oct. 2004), 488-493.
Escott, Benjamin G, et al., "NeuFlex and Swanson Metacarpophalangeal Implants for Rheumatoid Arthritis: Prospective Randomized, Controlled Clinical Trial", The Journal of hand surgery 35(1), (Jan. 2010), 44-51.
Fitzpatrick, Dan C, et al., "Relative Stability of Conventional and Locked Plating Fixation in a Model of the Osteoporotic Femoral Diaphysis", Journal of Clinical Biomechanics 24(2), (Feb. 2009), 203-209.
Foliart, Donna E, "Synovitis and silicone joint implants: a summary of reported cases", Journal of Plastic and Reconstructive Surgery 99(1), (Jan. 1997), 245-252.
Gaggl, A, et al., "Biomechanical properties in titanium implants with integrated maintenance free shock absorbing elements", Journal of Biomaterials 22(2001), (Nov. 15, 2001), 3061-3066.
Gard, S. A, et al., "The effect of a shock-absorbing pylon on the gait of persons with unilateral transtibial amputation.", Journal of Rehabilitation Research and Development 40(2), (2003), 109-124.
Gracis, S. E, et al., "Shock absorbing behavior of five restorative materials used on implants.", The International journal of prosthodontics 4(3), (Jan. 1992), 282-291.
Rockwood, Charles A, et al., "", Rockwood and Green's fractures in adults, Lippincott Company, (Jan. 1, 1991), 16 pgs.
"U.S. Appl. No. 16/689,703, Non Final Office Action dated Aug. 31, 2021", 6 pgs.
"U.S. Appl. No. 16/689,703, Response filed Nov. 30, 2021 to Non Final Office Action dated Aug. 31, 2021", 9 pgs.
"Chinese Application Serial No. 201810151451.3, Decision of Rejection dated Mar. 16, 2021", (W/ English Translation), 13 pgs.
"Chinese Application Serial No. 201810151451.3, Office Action dated Oct. 23, 2020", (W/English Translation), 10 pgs.
"Chinese Application Serial No. 201810151451.3, Response filed Jan. 7, 2021 to Office Action dated Oct. 23, 2020", (W/ English Translation of Claims), 7 pgs.

(56) References Cited

OTHER PUBLICATIONS

"U.S. Appl. No. 16/689,703, Final Office Action dated Dec. 13, 2021", 5 pages.
"U.S. Appl. No. 16/689,703, Notice of Allowance dated Mar. 31, 2022", 8 pgs.

* cited by examiner

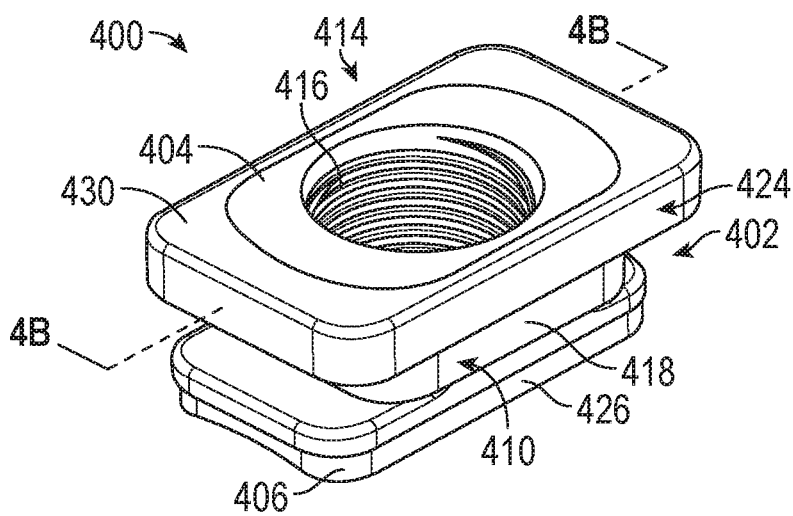
FIG. 4A
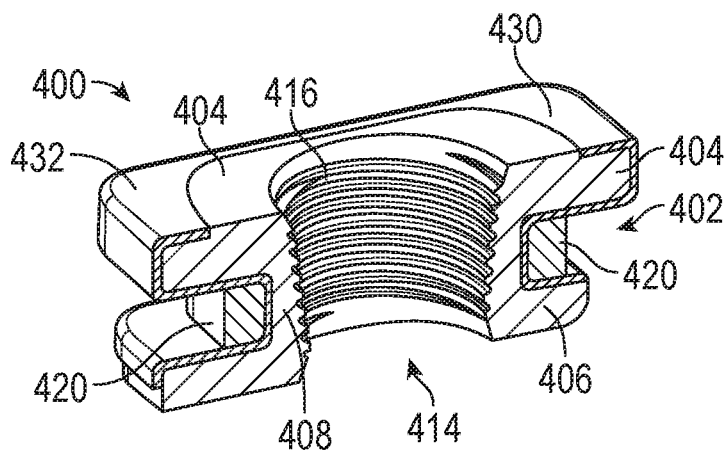
FIG. 4B
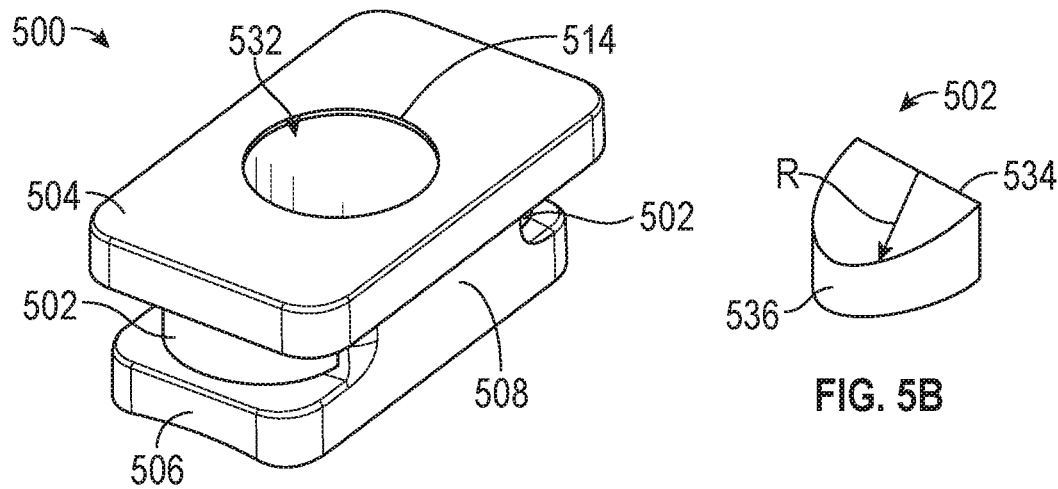
FIG. 5A
FIG. 5B

ACTIVE BONE PLATE

PRIORITY CLAIM

This application claims the benefit of priority to U.S. Provisional Patent Application Ser. No. 62/943,321, filed on Dec. 4, 2019, and entitled "Active Bone Plate," which is hereby incorporated by reference herein in its entirety.

FIELD OF THE DISCLOSURE

The present disclosure relates to bone plates. Specifically, the present disclosure relates to active bone plates and methods of use thereof.

BACKGROUND

Bone plates are used in a variety of surgical procedures, such as to treat fractures of bones in the body. For example, an elongate bone plate with a plurality of fixation holes along its extent can be used to affix the bone plate to multiple bone fragments of a fractured bone. The bone plate bridges the gaps created between bone fragments to provide support for the fractured bone and aiding in the healing process.

SUMMARY

The following, non-limiting examples, detail certain aspects of the present subject matter to solve the challenges and provide the benefits discussed herein, among others.

Example 1 is a bone plate comprising: a plate frame having a first surface, the plate frame defining a first opening and a second opening along a longitudinal axis that extends from opposing ends of the plate frame; and a first anvil and a second anvil, the first and second anvils each comprising: a first plate having a first surface arranged to rest against the first surface of the plate frame when the bone plate is implanted, a second plate sized to pass into each of the first and second openings, and a body located in between the first and second plates, the body defining a through hole sized to receive a fastener, the body sized such that the plate frame is moveable along the longitudinal axis relative to the first and second anvils when the bone plate is implanted.

In Example 2, the subject matter of Example 1 optionally includes wherein the first surface of the plate frame defines a recess sized to receive the first plate of each of the first and second anvils.

In Example 3, the subject matter of any one or more of Examples 1-2 optionally include wherein the plate frame defines first and second locking pin holes and the first plate of each of the first and second anvils defines a complementary locking pin hole.

In Example 4, the subject matter of any one or more of Examples 1-3 optionally include wherein the first anvil is manufactured from a metal and includes a polymer cladding.

In Example 5, the subject matter of any one or more of Examples 1-4 optionally include wherein the plate frame includes first and second flexible tabs projecting into the first and second openings, respectively, and wherein the second plate of each of the first and second anvils includes first and second beveled flanges configured to engage the first and second flexible tabs, respectively.

In Example 6, the subject matter of any one or more of Examples 1-5 optionally include wherein the through hole of the first anvil is unthreaded so as to receive a compression screw.

In Example 7, the subject matter of any one or more of Examples 1-6 optionally include wherein the through hole of the second anvil is threaded so as to receive a locking screw.

In Example 8, the subject matter of any one or more of Examples 1-7 optionally include wherein the second plate of the first and second anvils each protrudes below a second surface of the plate frame when implanted, the second surface of the plate frame located opposite the first surface of the plate frame.

In Example 9, the subject matter of any one or more of Examples 1-8 optionally include wherein the first and second openings are rectangular.

In Example 10, the subject matter of any one or more of Examples 1-9 optionally include wherein the first anvil includes a first gasket and the second anvil includes a second gasket.

In Example 11, the subject matter of Example 10 optionally includes wherein the first gasket has a first resiliency and the second gasket has a second resiliency, the first resiliency being greater than the second resiliency.

In Example 12, the subject matter of any one or more of Examples 10-11 optionally include wherein the first gasket has a first resiliency and the second gasket has a second resiliency, the first resiliency and the second resiliency being equal.

Example 13 is a bone plate system comprising: a plate frame having a first surface and a longitudinal axis extending between opposed first and second ends of the plate frame, the plate frame defining a plurality of openings; a plurality of fasteners; and a plurality of anvils, each of the plurality of anvils comprising: a first plate having a first surface arranged to rest against the first surface of the plate frame when the plate frame is implanted, a second plate sized to pass through at least one of the plurality of openings, and a body located in between the first plate and the second plate, the body defining a through hole sized to receive one of the plurality of fasteners, the body sized such that, when implanted, the body is moveable along the longitudinal axis of the plate frame.

In Example 14, the subject matter of Example 13 optionally includes a plurality of locking pins, the plate frame defining a plurality of locking pin holes and the first plate of each of the plurality of anvils defining a complementary locking pin hole.

In Example 15, the subject matter of any one or more of Examples 13-14 optionally include wherein the plate frame includes a plurality of flexible tabs, each of the plurality of flexible tabs projecting into a corresponding one of the plurality openings, and wherein the second plate of each of the plurality of anvils includes a beveled flange configured to engage one of the plurality of flexible tabs.

In Example 16, the subject matter of any one or more of Examples 13-15 optionally include wherein the second plate of at least one of the plurality of anvils protrudes below a second surface of the plate frame when implanted, the second surface of the plate frame located opposite the first surface of the plate frame.

In Example 17, the subject matter of any one or more of Examples 13-16 optionally include wherein a first subset of the plurality of anvils is a first size and a second subset of the plurality of anvils is a second size, the first and second sizes being different.

In Example 18, the subject matter of any one or more of Examples 13-17 optionally include wherein each of the plurality of anvils includes a gasket.

In Example 19, the subject matter of Example 18 optionally includes wherein the gasket of a first one of the plurality of anvils has a first resiliency and the gasket of a second one of the plurality of anvils has a second resiliency, the first resiliency being different than the second resiliency.

In Example 20, the subject matter of any one or more of Examples 18-19 optionally include wherein the gasket of a first one of the plurality of anvils has a first resiliency and the gasket of a second one of the plurality of anvils has a second resiliency, the first resiliency and the second resiliency being equal.

In Example 21, a bone plate or a bone plate system of any one or any combination of Examples 1-20 can optionally be configured such that all elements or options recited are available to use or select from.

BRIEF DESCRIPTION OF THE FIGURES

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

FIGS. 4A and 4B show an anvil and a gasket in accordance with at least one example of the present disclosure.

FIGS. 5A and 5B show an anvil and a gasket in accordance with at least one example of the present disclosure.

Corresponding reference characters indicate corresponding parts throughout the several views. The exemplifications set out herein illustrate exemplary embodiments of the disclosure, and such exemplifications are not to be construed as limiting the scope of the disclosure any manner.

DETAILED DESCRIPTION

In bone fracture treatments a nailing approach can promote secondary bone healing and can create a faster and stronger bone healing since there is a relative motion of diaphysis bone fragments that can stimulate the remodeling tissue. Traditional bone plates do not allow for the relative motion of diaphysis bone. The bone plates and bone plate systems disclosed herein allow for relative motion of diaphysis bone. To allow for relative motion of the diaphysis bone, the bone plates and bone plate systems disclosed herein incorporate at least axial displacement between screws that are used to hold a plate frame in place and the plate frame.

The bone plates, bone plate systems, and method of use thereof disclosed herein include a bone plate that includes a plate frame and a plurality of anvils. The plate frame can have a first surface for the anvils to rest against. The plate frame can also define a plurality of openings. Each of the plurality of openings can accept one of the plurality of anvils. Each of the plurality of anvils can have a size that is smaller than the plurality of openings so as to pass through the openings.

When the bone plate is attached to bone or otherwise implanted within a patient, the plate frame can move relative to the plurality of anvils. For example, each of the anvils can include a gasket that can fill any space between the anvils and the openings. The gasket can be a resilient material that can allow for movement of the anvils relative to the plate frame. Stated another way, the gasket can allow for a dynamic response to loading, such as, for example, allowing for dampening or a delayed response to moderate impacts such as high-speed loads and slow ramping loads. Non-limiting examples of resilient materials can include elastomers, silicones, and materials that can respond with a viscoelastic behavior to physiological loading conditions.

The movement of the anvils relative to the plate frame can allow for bone fragments to move. The movement of bone fragments, which does not occur with traditional bone plates, can stimulate bone growth to promote faster healing. Stated another way, the bone plate systems disclosed herein can allow for movement of anvils, and bone fragments in a predefined direction with compression of the bone fragments.

The above discussion is intended to provide an overview of subject matter of the present patent application. It is not intended to provide an exclusive or exhaustive explanation of the embodiments disclosed herein. The description below is included to provide further information about the embodiments.

Figure 1A:
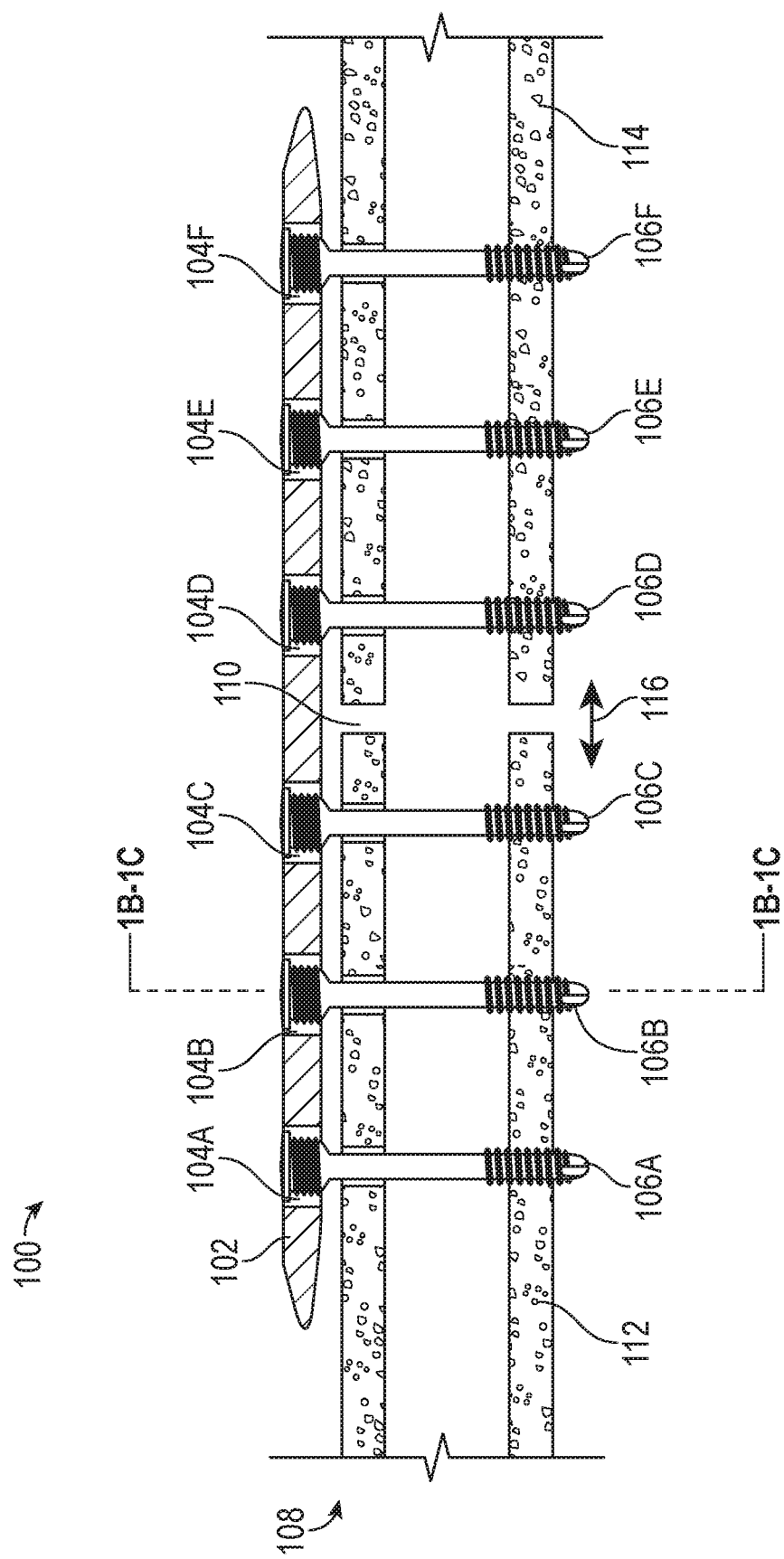
FIGS. 1A, 1B, and 1C show a bone plate system in accordance with at least one example of the present disclosure.
Figure 1B:
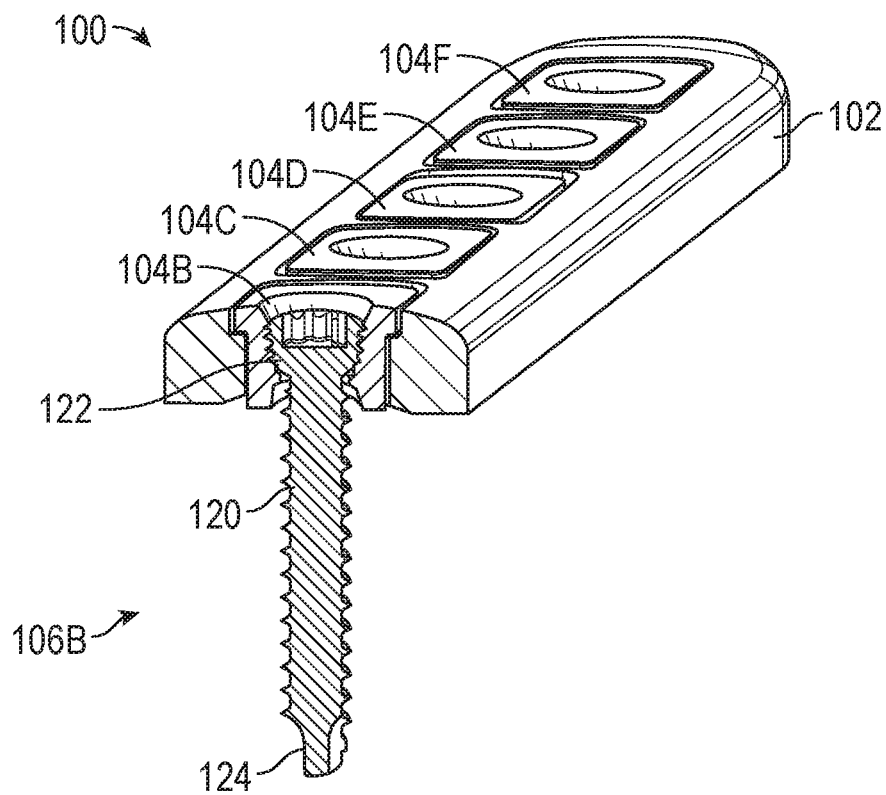
Figure 1C:
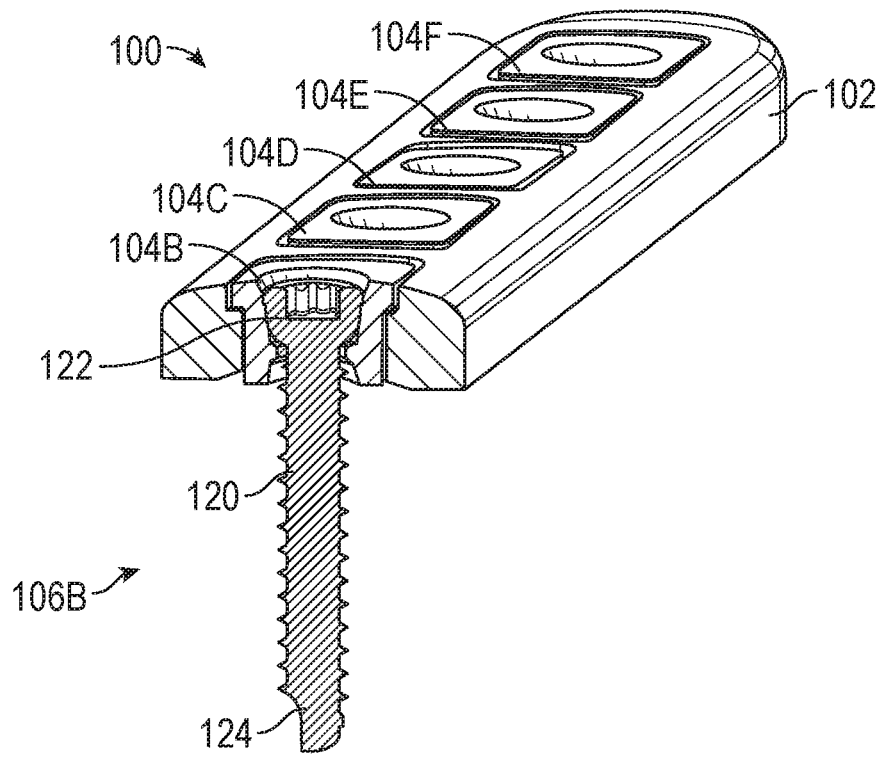

FIGS. 1A, 1B, and 1C illustrate a bone plate system 100, in accordance with at least one example of this disclosure. Bone plate system 100 can include a plate frame 102, anvils 104 (labeled individually as anvil 104A, 104B, 104C, 104D, 104E, and 104F), and fasteners such as screws 106 (labeled individually as screw 106A, 106B, 106C, 106D, 106E, and 106F). As shown in FIG. 1A, when implanted, screws 106 can pass through anvils 104 and into a bone 108. As shown in FIGS. 1B and 1C, screws 106 can include a shaft 120, a head 122, and a self-tapping portion 124. During insertion, the self-tapping portion can cut threads into bone 108 as shaft 120 passes into bone 108. Head 122 can rest in anvil 104B. In addition, screws 106 can be insertable in a polyaxial manner. For instance, screws 106 can each be inserted at an angle relative to a hole in anvils 104 through which they pass and at an angle relative to one another.

Bone 108 can have a bone gap 110. Bone gap 110 can be caused by a fracture or other trauma that caused bone 108 to be separated into a first bone fragment 112 and a second bone fragment 114. Bone gap 110 is shown exaggerated in FIG. 1A. Once bone plate system 100 is implanted first bone fragment 112 and second bone fragment 114 can be in contact with one another.

As shown in FIG. 1A, first bone fragment 112 and second bone fragment 114 can be moveable as indicated by arrow 116. First bone fragment 112 and second bone fragment 114 can be compressed against one another using bone plate system 100. As disclosed herein, compression of first bone fragment 112 and second bone fragment 114 along with movement of first bone fragment 112 and second bone fragment 114 can promote healing of the bone 108.

Figure 2A:
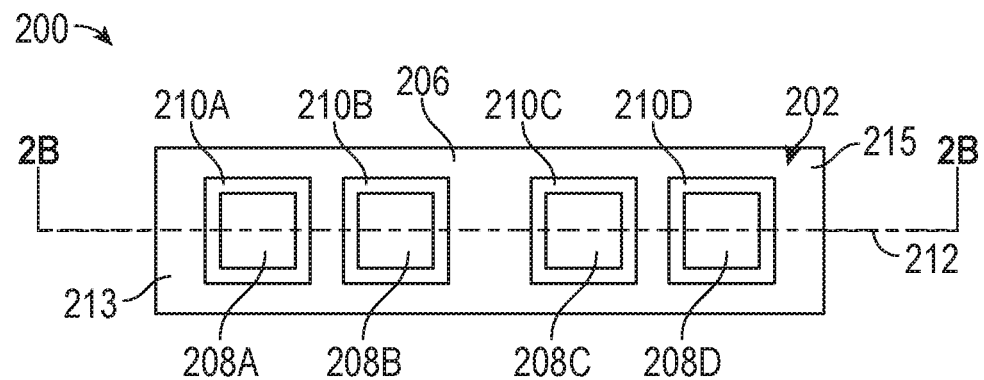
FIGS. 2A, 2B, and 2C show a plate frame in accordance with at least one example of the present disclosure.
Figure 2B:
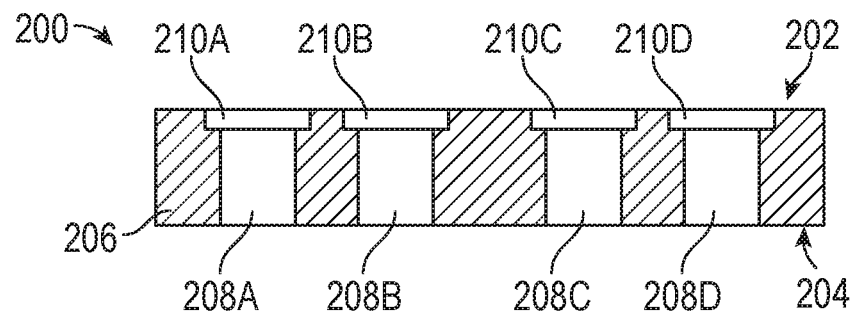

FIGS. 2A and 2B show a plate frame 200, similar to plate frame 102, in accordance was at least one example of the present disclosure. The plate frame 200 can include a first surface 202 and a second surface 204. The second surface 204 can be located opposite the first surface 202. A body 206 of the plate frame 200 can define openings 208 (labeled individually as opening 208A, 208B, 208C, and 208D). The openings 208 can pass through plate frame 200. Plate frame 200 can also define recesses 210 (labeled individually as recess 210A, 210B, 210C, and 210D). Recesses 210 can allow a first plate of anvils disclosed herein to rest substantially flush with or beneath first surface 202. Alternatively, or in addition, a second plate of anvils disclosed herein can pass through openings 208 and protrude below second surface 204 as disclosed herein with respect to at least FIG. 7.

Figure 2C:
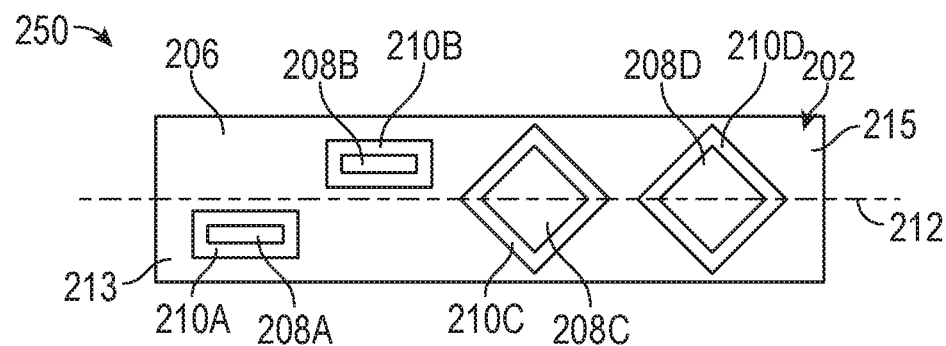

While FIGS. 2A and 2B show openings 208 arranged along a longitudinal axis 212 that extends from opposing first and second ends 213 and 215 of body 206, openings 208 can be arranged staggered to longitudinal axis 212 as shown in FIG. 2C. In addition, while FIGS. 2A and 2B show openings 208 arranged perpendicular to longitudinal axis 212, openings 208 can be arranged at an angle relative to longitudinal axis 212 as shown in FIG. 2C.

FIG. 2C shows a plate frame 2250 that includes openings 208 and recesses 210. Openings 208 and 210 can be square or rectangular as shown in FIG. 2C. In other examples, openings 208 and recesses 210 can be a curved shape such as a circle or an oval. In yet other examples, openings 208 and recesses 210 can define any symmetrical or asymmetrical shape. Plate frame 200 can include a combination of square and rectangular openings 208 and recesses 210. An opening does not have to have a recess. For example, opening 208A can have recess 210A while opening 208B does not have to have recess 210B. While FIGS. 2A, 2B, and 2C show recesses 210 having the same shape as openings 208, recesses 210 do not have to have the same shape as openings 208. For example, openings 208 may be circular and recesses 210 may be square.

When implanted, longitudinal axis 212 can be arranged parallel to arrow 116 (FIG. 1A). Orienting longitudinal axis 212 parallel to arrow 116 can allow for movement of first bone fragment 112 and second bone fragment 114 in a predefined direction. Stated another way, anvils 104 can be fixed to bone 108 via screws 106 and move relative to plate frame 102. The movement of anvils 104 can be constrained along longitudinal axis 212 as disclosed herein.

As disclosed herein, plate frame 102 and anvils 104 can constrain movement of first bone fragment 112 and second bone fragment 114 along longitudinal axis 212 while also preventing movement of first bone fragment 112 and second bone fragment 114 in a direction perpendicular to longitudinal axis 212. The constriction of movement can allow first bone fragment 112 and second bone fragment 114 to be preloaded in contact with one another while preventing lateral movement that can cause additional damage to bone 108. Stated another way, by constricting movement of first bone fragment 112 and second bone fragment 114 to only movement along longitudinal axis 212, first bone fragment 112 and second bone fragment 114 can be prevented from grinding against one another.

Also, need to add some language to the spec, and maybe the claims, that the plate is constrained/prevented from any substantial movement in a direction perpendicular to the longitudinal axis. I believe that is an important aspect of these active plate designs from my prior experience.

Plate frame 200 can be manufactured from a metal, polymer, ceramic, or any combination thereof. For example, plate frame 200 can be machined, cast, etc. from a metal. Plate frame 200 can be injection molded from a polymer. Plate frame 200 can be machined from a metal and then coated with a polymer cladding via an overmolding process.

Figure 3A:
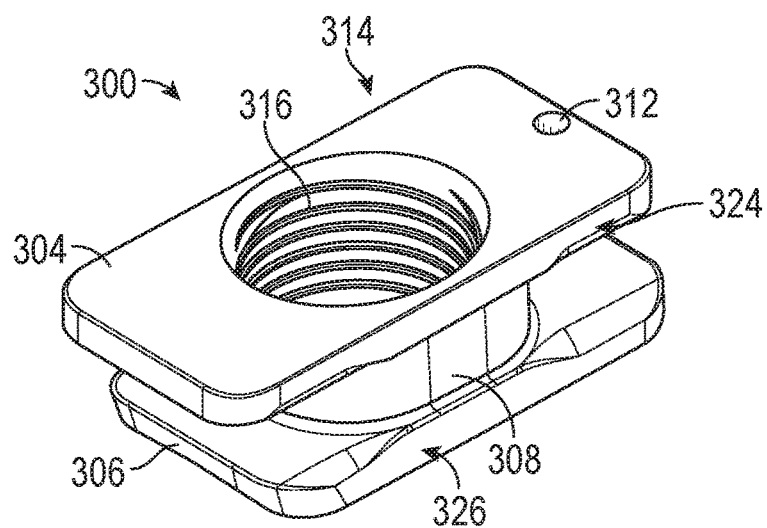
FIGS. 3A, 3B, and 3C show an anvil and a gasket in accordance with at least one example of the present disclosure.
Figure 3B:
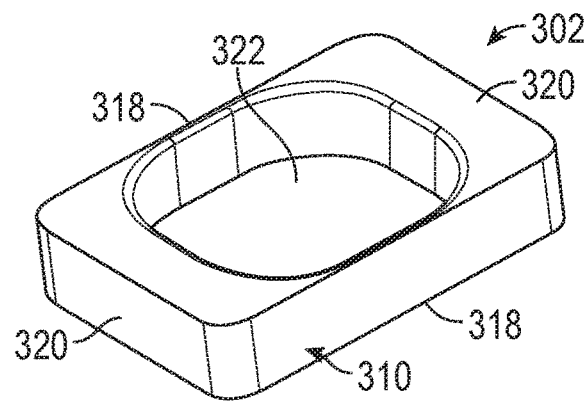
Figure 3C:
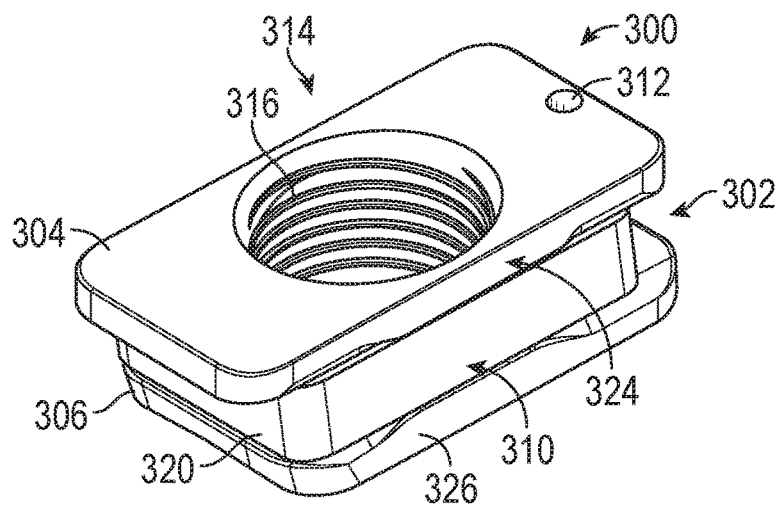

FIGS. 3A, 3B, and 3C show an anvil 300 and a gasket 302 in accordance with at least one example of the present disclosure. Anvil 300 can include a first plate 304, a second plate 306, and a body 308 located in between first plate 304 and second plate 306. First plate 304 and second plate 306 can be the same size or different sizes. For example, as shown in FIG. 3C, first plate 304 can extend past an exterior surface 310 of gasket 302. The larger size of first plate 304 can allow a portion of first plate 304 to rest on a surface of a plate frame, such as plate frame 102 or plate frame 200, while allowing body 308 and second plate 306 to rest in an opening, such as any one of openings 208. First plate 304 can also define a locking hole 312. As disclosed herein, locking hole 312 can be used to lock anvil 300 to a plate frame while implanting a bone plate.

Body 308 can define a through hole 314. Through hole 314 can receive a fastener, such as one of screws 106. For example, through hole 314 can allow for compression screws and locking screws to pass through anvil 300 to secure anvil 300 to a bone or bone fragment. For instance, through hole 314 can include threads 316 to engage a locking screw to secure anvil 300 to a bone or bone fragment.

Anvil 300 can be manufactured from a metal, polymer, ceramic, or any combination thereof. For example, anvil 300 can be machined, cast, etc. from a metal. Anvil 300 can be injection molded from a polymer. Anvil 300 can be machined from a metal and then coated with a polymer or ceramic cladding.

Gasket 302 can be manufactured from a polymer or other flexible material. As shown in FIG. 3B, side portions 318 can be thinner than end portions 320 and define a through hole 322. The thin and flexible nature of side portions 318 can allow gasket 302 to stretch and be slid over either first plate 304 or second plate 306. Once clear of first plate 304 or second plate 306, gasket 302 can encircle body 308 and rest in between first plate 304 and second plate 306. Side portions 318 can rest flush with sidewalls 324 and 326 of first plate 304 and second plate 306. Sidewalls 324 and 326 can protrude past exterior surface 310 of gasket 302.

FIGS. 4A and 4B show an anvil 400 and a gasket 402 in accordance with at least one example of the present disclosure. Anvil 400 can include a first plate 404, a second plate 406, and a body 408 located in between first plate 404 and second plate 406. First plate 404 and second plate 406 can be the same size or different sizes as described above with respect to FIGS. 3A, 3B, and 3C. The larger size of first plate 404 can allow a portion of first plate 404 to rest on a surface of a plate frame, such as plate frame 102 or plate frame 200, while allowing body 408 and second plate 406 to rest in an opening, such as any one of openings 208.

Body 408 can define a through hole 414. Through hole 414 can receive a fastener, such as one of screws 106. For example, through hole 414 can allow for compression screws and locking screws to pass through anvil 400 to secure anvil 400 to a bone or bone fragment. For instance, through hole 414 can include threads 416 to engage a locking screw to secure anvil 400 to a bone or bone fragment.

Anvil 400 can be manufactured from a metal, polymer, ceramic, or any combination thereof. For example, anvil 400 can be machined, cast, etc. from a metal. Anvil 400 can be injection molded from a polymer. As shown in FIGS. 4A and 4B, anvil 400 can include a cladding 430. Cladding 430 can be a polymer, metal, ceramic, or any combination thereof.

Consistent with embodiments disclosed herein, cladding 430 can be a different material from a plate frame. For example, cladding 430 can be a polymer that is overmolded onto a metal anvil. The polymer cladding 430 can include a lubricated polymer or other wear resistant material. As such, movement of anvil 400 against a metal plate frame can minimize damage to anvil 400 and the plate frame. Stated another way, cladding 430 can eliminate metal on metal contact, which can cause wear and damage the bone plate. As one example, cladding 430 can be a polyether ether ketone (PEEK) applied to bearing surfaces to allow anvil 400 to slide against surfaces of the plate frame.

Gasket 402 can be manufactured from a polymer or other flexible material. As disclosed above with respect to FIG. 3B, side portion 418 can be thinner than end portions 420 and define a through hole as described herein. The thin and flexible nature of side portions 418 can allow gasket 402 to stretch and be slid over either first plate 404 or second plate 406. Once clear of first plate 404 or second plate 406, gasket 402 can encircle body 408 and rest in between first plate 404 and second plate 406. Side portions 418 can rest flush with sidewalls 424 and 426 of first plate 404 and second plate 406. Sidewalls 424 and 426 can protrude past exterior surface 410 of gasket 402.

FIGS. 5A and 5B show an anvil 500 and gaskets 502 in accordance with at least one example of the present disclosure. Anvil 500 can include a first plate 504, a second plate 506, and a body 508 located in between first plate 504 and second plate 506. First plate 504 and second plate 506 can be the same size or different sizes as described above with respect to FIGS. 3A, 3B, and 3C. The larger size of first plate 504 can allow a portion of first plate 504 to rest on a surface of a plate frame, such as plate frame 102 or plate frame 200, while allowing body 508 and second plate 506 to rest in an opening, such as any one of openings 208.

Body 508 can define a through hole 514. Through hole 514 can receive a fastener, such as one of screws 106. For example, through hole 514 can allow for compression screws and locking screws to pass through anvil 400 to secure anvil 400 to a bone or bone fragment. For instance, through hole 514 can include a smooth surface 532 to allow a compression screw to engage anvil 500. A non-threaded hole, such as through hole 514, that includes a PEEK cladding (or anvil 500 is made from PEEK) can allow for a threaded head screw to be installed in a custom orientation. For example, the threads on the head of the screw can cut their own threads into the PEEK as the surgeon drives the screw into bone.

Anvil 500 can be manufactured from a metal, polymer, ceramic, or any combination thereof. For example, anvil 500 can be machined, cast, etc. from a metal. Anvil 500 can be injection molded from a polymer. Anvil 500 can include a cladding as described above with respect to FIGS. 4A and 4B. Making anvil 500 from a polymer can include making anvil 500 from a lubricated polymer or other wear resistant material. As such, movement of anvil 500 against a metal plate frame can minimize damage to anvil 500 and the plate frame. The plate frame can be made of a polymer and anvil 500 can be made of a metal.

Gaskets 502 can be manufactured from a polymer or other flexible material. As shown in FIG. 5B, gaskets 502 can have a flat face 534 and a curved portion 536. Flat face 534 can include a mastic or other adhesive that can allow gaskets 502 to bond or otherwise adhere to body 508. Gaskets 502 can be made of the same material or different materials. For example, one of gaskets 502 can be made of a first material and the other gasket 502 can be made of a second material. The first material can have a first resiliency and the second material can have a second resiliency. The first resiliency and the second resiliency can be the same or different.

Both of gaskets 502 need not be present in every embodiment. For example, to increase a biasing force toward a bone gap, a gasket 502 can be attached to body 508 opposite the bone gap. As a result, gasket 502 can apply a force to the plate frame that pushes anvil 500 towards to bone gap. In another embodiment, gasket 502 can be attached to body 508 on the same side as the bone gap. As a result, gasket 502 can act as a shock absorber to minimize impact forces that may be created if bone fragments are permitted to hit one another under loading. For instance, when a patient walks, gasket 502 can act as a shock absorber to minimize impact forces generated in femur fragments generated when the patient's foot hits the floor.

Instead of or in addition to an adhesive used to attach gaskets 502 to body 508, the thickness of gaskets 502 can be such that friction is able to secure gaskets 502 in between first plate 504 and second plate 506. For example, if the distance between first plate 504 and second plate 506 is 5 mm, the thickness of gaskets 502 may be 5.5 mm. Thus, when gaskets 502 are pressed into the space formed by first plate 504, second plate 506, and body 508, friction can hold gaskets 502 in between first plate 504 and second plate 506.

The radius, R, of gaskets 502 can vary. For example, one of gaskets 502 can have a radius or $R_1$ and the other gasket 502 can have a radius of $R_2$. During surgery, the surgeon can select gaskets 502 to adjust the travel of anvil 500 within an opening of a plate frame. For instance, to increase the distance anvil 500 can move within an opening of a plate frame, gaskets 502 with a smaller radius can be selected. To decrease the distance anvil 500 can move within an opening of a plate frame, gaskets 502 with a larger radius can be selected.

Figure 6A:
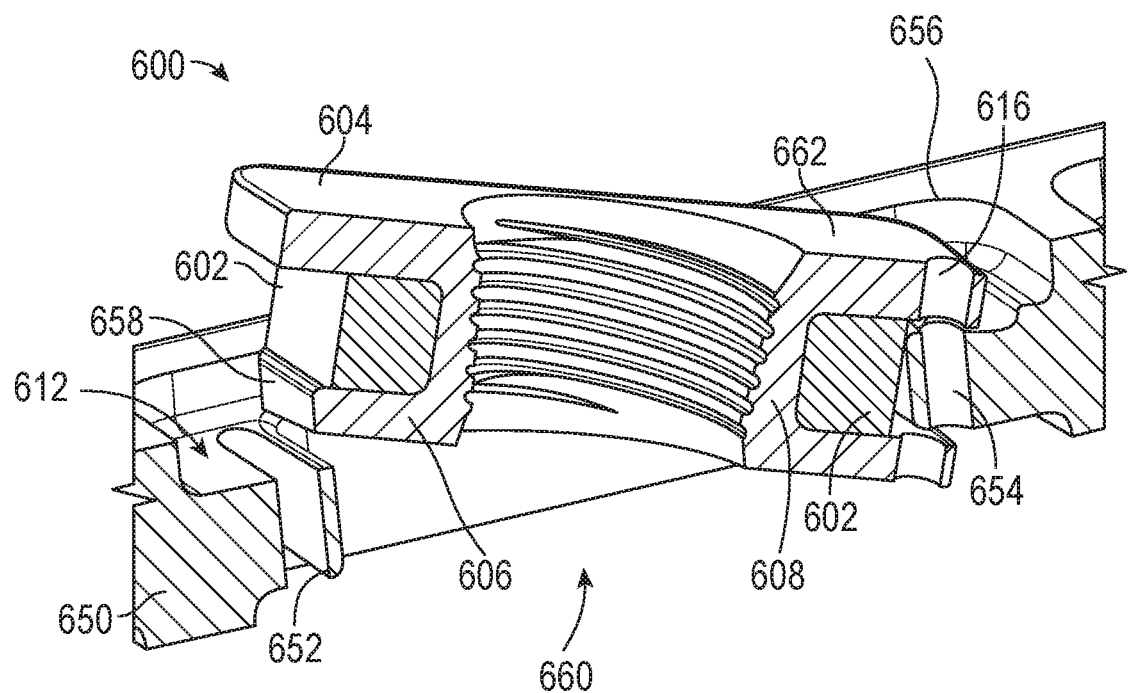
FIGS. 6A and 6B show the insertion of an anvil into a plate frame in accordance with at least one example of the present disclosure.
Figure 6B:
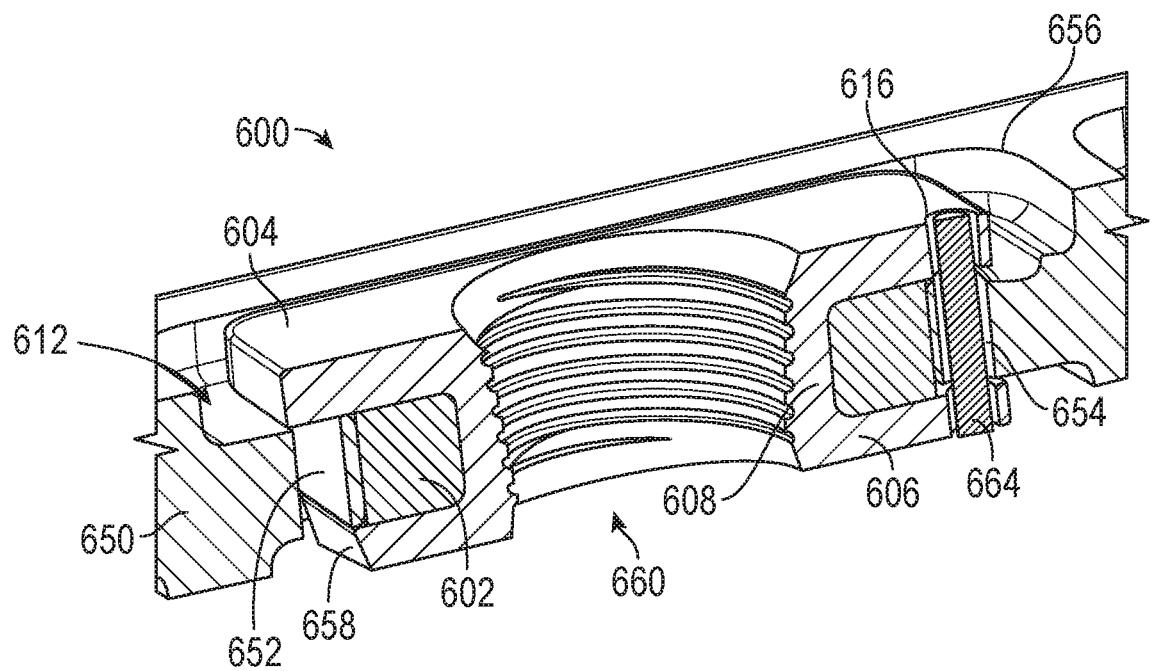

FIGS. 6A and 6B show the insertion of an anvil 600 into a plate frame 650 in accordance with at least one example of the present disclosure. Anvil 600 can include a gasket 602, a first plate 604, a second plate 606, and a body 608 located in between first plate 604 and second plate 606. Second plate 606 can include a beveled flange 658. During insertion of anvil 600 into an opening 660 a portion 662 of first plate 604 can rest against first surface 612. As anvil 600 rotates and second plate 606 enters opening 660, beveled flange 658 can contact flexible tab 652. The contact can cause flexible tab 652 to flex such that beveled flange 658 and second plate 606 pass flexible tab 652. Upon second plate 606 passing flexible tab 652, flexible tab 652 can be located in between first plate 604 and second plate 606 to retain anvil 600 in opening 660 as shown in FIG. 6B. Flexible tab 652 can rest against gasket 602 or there can be space in between flexible tab 652 and gasket 602.

Figure 7:
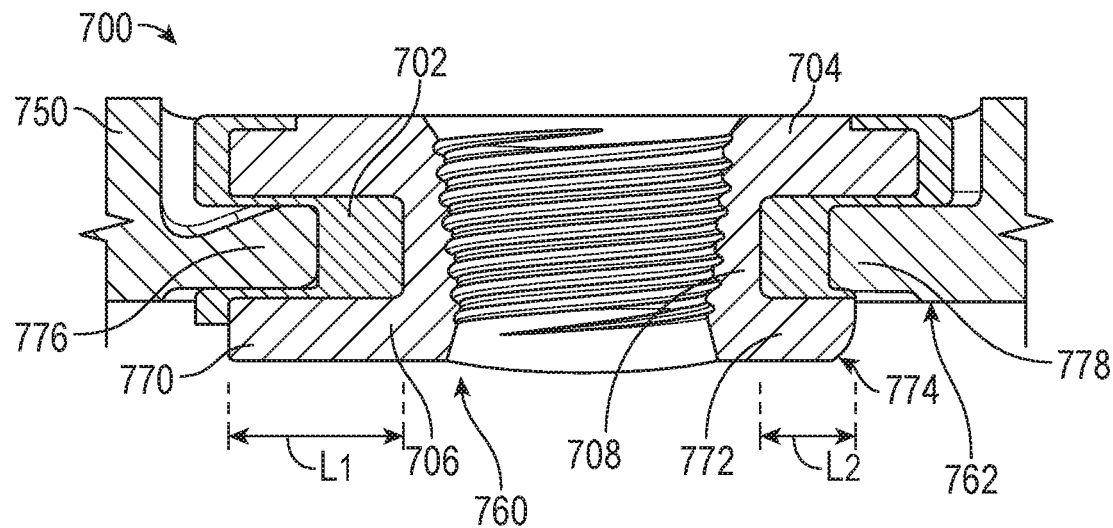
FIG. 7 shows an anvil inserted into a plate frame in accordance with at least one example of the present disclosure.

Plate frame 650 can define a locking pin hole 654 and a recess 656, Anvil 600 can define a complementary locking pin hole 616. As shown in FIG. 6B, a locking pin 664 can be inserted into locking holes 616 and 654, Insertion of locking pin 664 can restrict movement of anvil 600 within plate frame 650. The restriction of movement of anvil 600 can allow the surgeon to secure the anvil 600 to bone without anvil 600 moving. Having anvil 600 temporarily fixed to plate frame 650 can allow the surgeon to grip plate frame 650 instead of anvil 600, thereby decreasing the risk of slippage and possible injury to the patient and surgeon do to movement of anvil 600 and plate frame 650 while being attached to bone. Once anvil 600 is secured to bone, locking pin 664 can be removed to allow anvil 600 to move relative to plate frame 650, FIG. 7 shows an anvil 700 inserted into a plate frame 750 in accordance with at least one example of the present disclosure. Anvil 700 can include a gasket 702, a first plate 704, a second plate 706, and a body 708. As shown in FIG. 7, second plate 706 can include a first flange 770 and a second flange 772. First flange 770 can have a length, $L_1$, and second flange 772 can have a length $L_2$. $L_2$ can be less than $L_1$. Second flange 772 can include a curved surface 774. During insertion, gasket 702 can compressing against a first portion 776 of plate frame 750 and body 708 as curved surface 774 contacts and presses against a second portion 778 of plate frame 750. Upon clearing second portion 778, gasket 702 may decompress and press second flange 772 underneath second portion 778 to secure anvil 700 to plate frame 750.

As shown in FIG. 7, a bottom surface 760 of anvil 700 can protrude past a bottom surface 762 of plate frame 750. Having bottom surface 760 extend past bottom surface 762 can allow anvil 700 to be fixed to bone without having plate frame 750 also contact bone. Thus, by having bottom surface 760 extend past bottom surface 762, anvil 700 and bone attached to anvil 700 can move without causing plate frame 750 to rub against bone. Minimizing contact between plate frame 750 and bone can reduce a risk of further damage to bone that can be cause by plate frame 750 rubbing against bone or bone fragments as they move.

Further shown in FIG. 7, gasket 702 can extend and cover portions of first plate 704 and second plate 706. As a result, gasket 702 can act as a cladding, such as cladding 430 described above with respect to FIGS. 4A and 4B.

Figure 8:
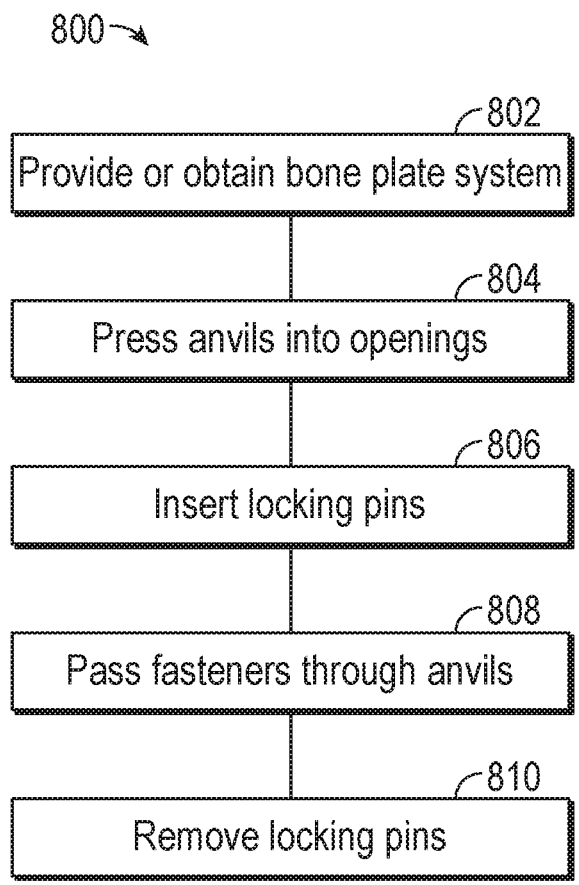
FIG. 8 shows a method in accordance with at least one example of the present disclosure.

FIG. 8 shows a method 800 in accordance with at least one example of the present disclosure. Method 800 can begin by providing or obtaining a bone plate system (802). Providing or obtaining a bone plate system can include providing or obtaining plate frames, anvils, fasteners, gaskets, etc. described herein, Providing or obtaining a bone plate system can include providing or obtaining anvils that include gaskets preinstalled or gaskets that are separate from the anvils. As such, the surgeon can select the gaskets and anvils as needed. The fasteners can include locking screws and compression screws. Multiple plate frames can be provided or obtained and the plate frames can include differing numbers of openings, different arrangement of the openings, etc.

During surgery the surgeon or other medical staff can press anvils into openings of plate frame(s) so that a plate of each of the anvils rests against a first surface of the plate frame(s) (804). For example, after the surgeon selects the anvils and plate frame(s) needed for the surgery, the anvils can be pressed into the plate frame(s) as disclosed herein. Pressing the anvils into the openings can include pressing the anvils such that a bottom surface of the anvils protrudes below a bottom surface of the plate frame(s) as disclosed herein. Pressing the anvils into the plate frame(s) can include pressing a first plate of the anvils into recesses in the plate frame(s) as disclosed herein.

Once the anvils are pressed into openings of the plate frame(s), locking pins can be inserted into locking pin holes in the anvils and plate frame(s) (806). As disclosed herein, inserting the locking pins can immobilize the anvils within the openings. Immobilizing the anvils can reduce the risk of injury to the surgeon, patient, and other medical staff by increasing the surface area in which the surgeon and medical staff can grip the plate frame(s).

After the locking pins are installed, fasteners can be passed through each of the anvils to secure the plate frame(s) to the bone (808). For example, to secure the plate frame(s) to the bone, the surgeon can drill holes into the bone and screw locking and compression screws through the anvils and into the drilled holes in the bone.

Once the plate frame(s) and anvils have been secured to the bone, the locking pin can be removed from the locking pin holes. By removing the locking pins, the anvils can be freed to move relative to the plate frame(s). For example, once the locking pins are removed the anvils can translate along a longitudinal axis of the plate frame(s).

The various stages of method 800 have been described in a particular order for ease of discussion and completeness. However, the various stages of method 800 can be rearranged and/or omitted without departing from the scope of the present disclosure. For example, inserting and removing the locking pins (stages 806 and 810) need not be completed.

NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A bone plate comprising:
   a plate frame having a first surface, the plate frame defining a first opening and a second opening along a longitudinal axis that extends from opposing ends of the plate frame; and
   a first anvil and a second anvil, the first and second anvils each comprising:
      a first plate having a first surface arranged to rest against the first surface of the plate frame when the bone plate is implanted,
      a second plate sized to pass into each of the first and second openings, and
      a body located in between the first and second plates, the body defining a through hole sized to receive a fastener, the body sized such that the plate frame is moveable along the longitudinal axis relative to the first and second anvils when the bone plate is implanted,
   wherein the plate frame defines first and second locking pin holes and the first plate of each of the first and second anvils defines a complementary locking pin hole.

2. The bone plate of claim 1, wherein the first surface of the plate frame defines a recess sized to receive the first plate of each of the first and second anvils.

3. The bone plate of claim 1, wherein the first anvil is manufactured from a metal and includes a polymer cladding.

4. The bone plate of claim 1,
   wherein the plate frame includes first and second flexible tabs projecting into the first and second openings, respectively, and
   wherein the second plate of each of the first and second anvils includes first and second beveled flanges configured to engage the first and second flexible tabs, respectively.

5. The bone plate of claim 1, wherein the through hole of the first anvil is unthreaded so as to receive a compression screw.

6. The bone plate of claim 1, wherein the through hole of the second anvil is threaded so as to receive a locking screw.

7. The bone plate of claim 1, wherein the second plate of the first and second anvils each protrudes below a second surface of the plate frame when implanted, the second surface of the plate frame located opposite the first surface of the plate frame.

8. The bone plate of claim 1, wherein the first and second openings are rectangular.

9. The bone plate of claim 1, wherein the first anvil includes a first gasket and the second anvil includes a second gasket.

10. The bone plate of claim 9, wherein the first gasket has a first resiliency and the second gasket has a second resiliency, the first resiliency being greater than the second resiliency.

11. The bone plate of claim 9, wherein the first gasket has a first resiliency and the second gasket has a second resiliency, the first resiliency and the second resiliency being equal.

12. A bone plate system comprising:
   a plate frame having a first surface and a longitudinal axis extending between opposed first and second ends of the plate frame, the plate frame defining a plurality of openings;
   a plurality of fasteners;
   a plurality of anvils, each of the plurality of anvils comprising:
      a first plate having a first surface arranged to rest against the first surface of the plate frame when the plate frame is implanted,
      a second plate sized to pass through at least one of the plurality of openings, and
      a body located in between the first plate and the second plate, the body defining a through hole sized to receive one of the plurality of fasteners, the body sized such that, when implanted, the body is moveable along the longitudinal axis of the plate frame; and
   a plurality of locking pins, the plate frame defining a plurality of locking pin holes and the first plate of each of the plurality of anvils defining a complementary locking pin hole.

13. The bone plate system of claim 12,
   wherein the plate frame includes a plurality of flexible tabs, each of the plurality of flexible tabs projecting into a corresponding one of the plurality openings, and
   wherein the second plate of each of the plurality of anvils includes a beveled flange configured to engage one of the plurality of flexible tabs.

14. The bone plate system of claim 12, wherein the second plate of at least one of the plurality of anvils protrudes below a second surface of the plate frame when implanted, the second surface of the plate frame located opposite the first surface of the plate frame.

15. The bone plate system of claim 12, wherein a first subset of the plurality of anvils is a first size and a second subset of the plurality of anvils is a second size, the first and second sizes being different.

16. The bone plate system of claim 12, wherein each of the plurality of anvils includes a gasket.

17. The bone plate system of claim 16, wherein the gasket of a first one of the plurality of anvils has a first resiliency and the gasket of a second one of the plurality of anvils has a second resiliency, the first resiliency being different than the second resiliency.

18. The bone plate system of claim 16, wherein the gasket of a first one of the plurality of anvils has a first resiliency and the gasket of a second one of the plurality of anvils has a second resiliency, the first resiliency and the second resiliency being equal.

19. A bone plate comprising:
   a plate frame having a first surface, the plate frame defining a first opening and a second opening along a longitudinal axis that extends from opposing ends of the plate frame, the plate frame comprising a first flexible tab projecting into the first opening and a second flexible tab projecting into the second opening; and
   a first anvil and a second anvil, the first and second anvils each comprising:

a first plate having a first surface arranged to rest against the first surface of the plate frame when the bone plate is implanted, a second plate sized to pass into each of the first and second openings, the second plate including a beveled flange configured to engage the flexible tab of the first and second opening, respectively, and a body located in between the first and second plates, the body defining a through hole sized to receive a fastener, the body sized such that the plate frame is moveable along the longitudinal axis relative to the first and second anvils when the bone plate is implanted.

20. The bone plate of claim 19, wherein the first anvil includes a first gasket and the second anvil includes a second gasket, and the first gasket has a first resiliency and the second gasket has a second resiliency, the first resiliency and the second resiliency being equal.

* * * * *